(12) United States Patent
Strnad

(10) Patent No.: US 10,856,913 B2
(45) Date of Patent: Dec. 8, 2020

(54) ODONTOID BULLET

(71) Applicant: Intrepid Orthopedics, Richfield, OH (US)

(72) Inventor: Lee A Strnad, Richfield, OH (US)

(73) Assignee: INTREPID ORTHOPEDICS, Richfield, OH (US)

(*) Notice: Subject to any disclaimer, the term of this patent is extended or adjusted under 35 U.S.C. 154(b) by 0 days.

(21) Appl. No.: 16/036,504

(22) Filed: Jul. 16, 2018

(65) Prior Publication Data

US 2018/0325563 A1 Nov. 15, 2018

Related U.S. Application Data

(63) Continuation of application No. 15/224,629, filed on Jul. 31, 2016, now abandoned.

(60) Provisional application No. 62/199,961, filed on Jul. 31, 2015.

(51) Int. Cl.
*A61B 17/70* (2006.01)
*A61B 17/04* (2006.01)

(52) U.S. Cl.
CPC ...... *A61B 17/7062* (2013.01); *A61B 17/0401* (2013.01); *A61B 17/7053* (2013.01); *A61B 17/7059* (2013.01); *A61B 2017/0404* (2013.01); *A61B 2017/0409* (2013.01); *A61B 2017/0417* (2013.01)

(58) Field of Classification Search
CPC ............ A61B 17/7062; A61B 17/7053; A61B 17/7059; A61B 17/0401; A61B 2017/0404; A61B 2017/0459
See application file for complete search history.

(56) References Cited

U.S. PATENT DOCUMENTS

| | | | | |
|---|---|---|---|---|
| 8,876,900 | B2* | 11/2014 | Guederian | A61B 17/0401 623/13.14 |
| 2004/0254593 | A1* | 12/2004 | Fallin | A61B 17/0487 606/148 |
| 2010/0241164 | A1* | 9/2010 | Fischer | A61B 17/683 606/247 |
| 2012/0059416 | A1* | 3/2012 | Justin | A61B 17/0401 606/232 |

* cited by examiner

*Primary Examiner* — Julianna N Harvey
(74) *Attorney, Agent, or Firm* — Brainspark Associates, LLC

(57) ABSTRACT

Removeable and/or revisable fixation devices, systems and methods for repairing bone fractures via a single incision, including odontoid fractures to the C2 vertebral body, which incorporate an anchoring feature that crosses the fracture site to be positioned external to the fractured bone fragment and which provides compressive and radial forces externally to the bone to immobilize the bone fragment(s) for fixation to the main bone structure.

10 Claims, 24 Drawing Sheets

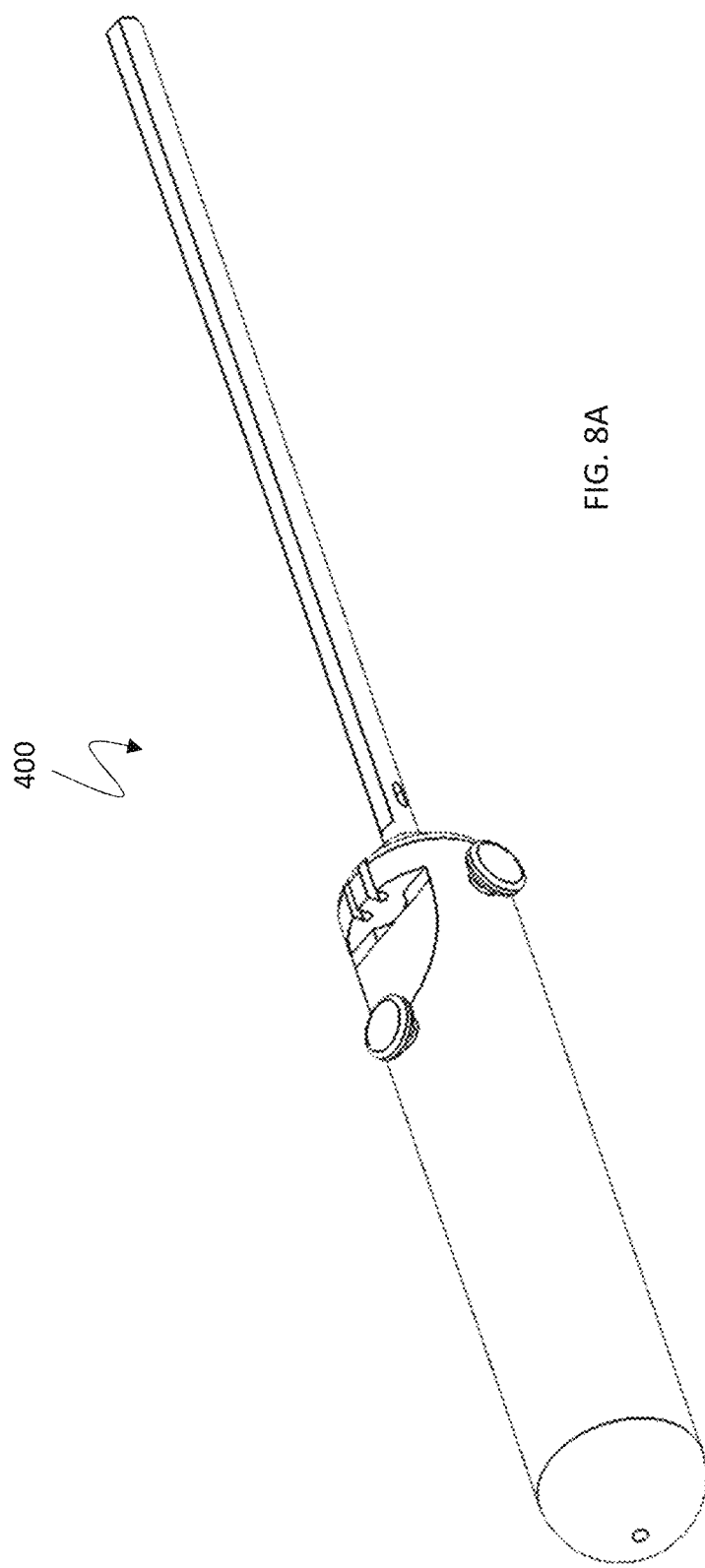

ODONTOID BULLET

CROSS-REFERENCE TO RELATED APPLICATIONS

This application is a continuation of U.S. patent application Ser. No. 15/224,629, filed Jul. 31, 2016 and entitled "Odontoid Bullet," which claims the benefit of U.S. Provisional Patent Application Ser. No. 62/199,961 entitled "ODONTOID BULLET," filed Jul. 31, 2015, the disclosure of which is incorporated by reference herein in its entirety.

TECHNICAL FIELD

The present invention relates generally to fixation and anchoring systems for surgical applications and, in particular, relates to an adjustable retaining system for anchoring bone fragments in spine surgery.

BACKGROUND

In order to effect natural healing of a fractured bone, the fractured portions of the bone must generally be kept together for a lengthy period of time in order to permit the recalcification and bonding of the fractured portions to the remaining bone. In many cases, adjoining portions of a fractured bone can be repositioned and maintained in an adjacent relationship (to allow healing of the bone) by being clamped together or otherwise attached to one another by means of a pin or a screw driven through the rejoined portions. In various areas of the body, such as in the cranium or spinal bones, fracture fixation can often experience a host of special problems and concerns due to the location of the bones, blood vessels, the spinal cord and other nerve tissues (and other anatomy) as well as the significant impact any injury can have on the patient, their rehabilitation and resulting quality of life issues. These issues can be further impacted by a physician's desire to remove fixation hardware after healing of the underlying anatomy has occurred, where the design of the fixation device and intervening scar tissue formation can potentially complicate and/or obviate subsequent removal of the device.

SUMMARY OF THE INVENTION

In accordance with various aspects of the present invention, devices, systems and methods are disclosed for treating odontoid fractures of the cervical spine. In various embodiments, a flexible tension member can be utilized in combination with a distal rotating anchor block or "bullet" type fastener and proximal anchor button to desirably compressively secure an odontoid fragment to the remaining bone of the C2 cervical bone.

In one exemplary embodiment, a distal bullet fixation device specifically adapted for treating odontoid fractures is disclosed herein. Desirably, the bullet device can be advanced through a passage or channel formed through the C2 body and the odontoid fragment (desirably crossing the fracture site), and then rotated to present an enlarged cross-section to the passage. A flexible fixation member attached to the bullet can then be tensioned, desirably drawing the odontoid fragment into intimate contact with the remaining C2 body. If desired, the flexible fixation member can be secured to a proximal anchor button, which secures and tensions the fixation member in a desired manner, thereby applying a compression force across the fracture site.

One aspect of the invention is directed to a cervical fixation system including: a "bullet" device having a reduced profile for advancement through a passage formed in the C2 body and one or more odontoid fragments. In various embodiments, the bullet could present a variety of surface profiles towards an odontoid fragment, including a concave shaped face for contacting an upper surface of the odontoid fragment. Desirably, the bullet and associated system components will draw one or more odontoid fragments towards the C2 vertebral body, fixating the fragment(s) in a desired fashion and applying compressive and/or radial forces across the fracture site.

In various embodiments, the bullet device can include revisability features that allow the bullet to be removed from the anatomy after healing of the injury has occurred (and/or if removal of the implant is desired for a variety of reasons). In at least one exemplary embodiment, the revisability feature can comprise a flexible cord or other feature attached proximate to an opening formed near one end of the bullet, which can be utilized to realign the longitudinal axis of the bullet with the passage and draw the bullet back through the passage or channel formed through the C2 body after the flexible fixation member is severed and/or otherwise detensioned.

In various embodiments, the disclosed devices, systems and components can be utilized with virtually all manner of odontoid fractures types, including Type I, Type II (A, B and C) and Type III. In addition, the disclosed devices can be utilized to treat odontoid fractures involving significant fracture displacement and/or angulation, as well as antero-inferior to postero-superior fractures (Type 2C fractures) that are currently untreatable and/or are treated using instrumented fusion of C1-C2.

BRIEF DESCRIPTION OF THE DRAWINGS

The foregoing and other objects, aspects, features, and advantages of embodiments will become more apparent and may be better understood by referring to the following detailed description of the preferred embodiments, taken in conjunction with the accompanying drawings, wherein:

FIGS. 8A through 8C depict one embodiment of an insertion tool and associated bullet and button;

DETAILED DESCRIPTION

Figure 1:
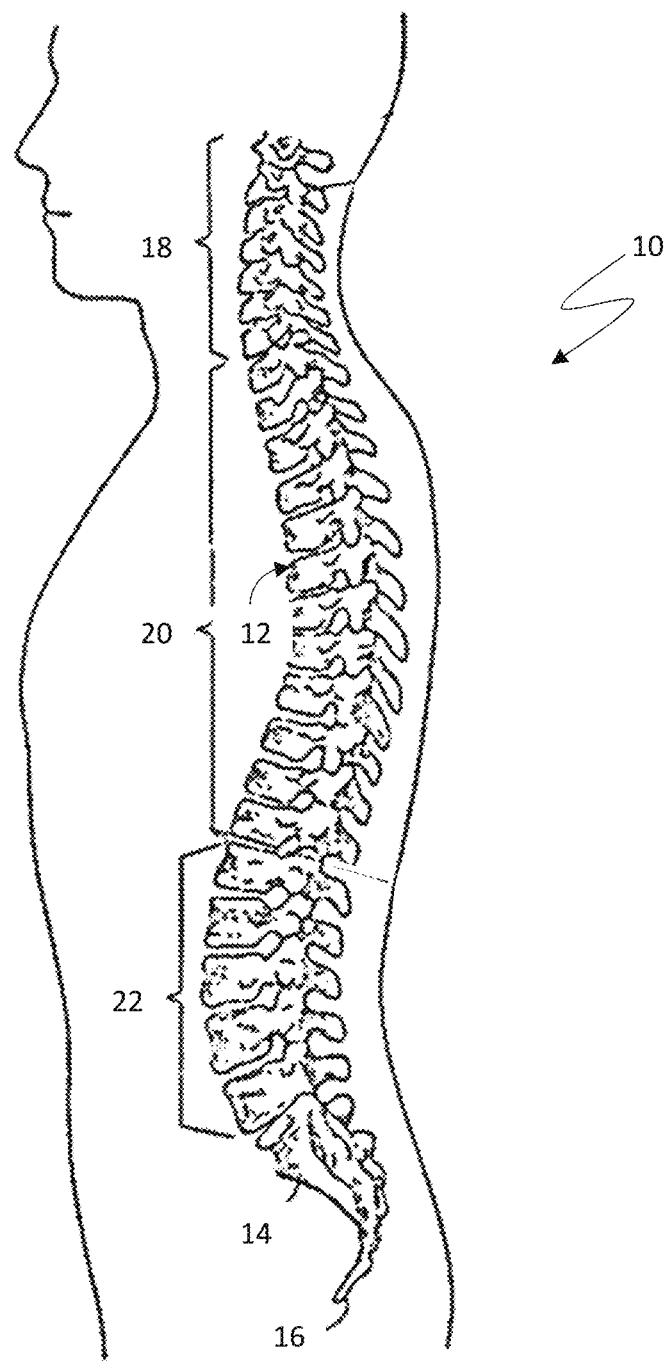
FIG. 1 depicts an exemplary spinal column.

Various features of the present invention include the recognition of a need for a more effective and versatile system of fixating and/or securing one or more odontoid bone fragments to an underlying C2 vertebrae. In addition, various features of the present invention include components that facilitate removal of fixation components from treated regions once healing has completed and/or in the event of implant failure or complications requiring implant removal and/or retreatment. A variety of configurations, sizes and shapes of such components and associated tools can be utilized in diverse anatomical regions, including use in cranial and/or spinal surgery as well as other anatomical locations. In various medical applications, the disclosed components and related surgical tools and techniques can desirably facilitate the treatment of various types of bone fractures by surgeons, which can be important to achieve the most accurate and best performance and/or fit of implant components and well as facilitate patient recovery.

This specification describes novel systems, devices and methods to treat spinal fractures. Aspects of the present invention will be described with regard to the treatment of vertebral bodies, e.g., odontoid fractures. It should be appreciated, however, that various aspects of the present invention may not limited in their application to odontoid fractures. The systems and methods may be applicable to the treatment of fractures in diverse bone types. Embodiments will now be described with reference to the drawings, wherein like reference numerals are used to refer to like elements throughout. It should be understood that the figures are not necessarily to scale.

FIG. 1 depicts an exemplary spinal column 10 of a human being. The spinal column 10 includes a number of uniquely shaped bones, called vertebrae 12, a sacrum 14, and a coccyx 16 (also called the tail bone). The number of vertebrae 12 that make up the spinal column 10 depends upon the species of animal. In a human, there are twenty-four vertebrae, comprising seven cervical vertebrae 18, twelve thoracic vertebrae 20, and five lumbar vertebrae 22.

When viewed from the side, as illustrated in FIG. 1, the spinal column 10 forms an S-shaped curve. The curve serves to support the head and upper torso. Each vertebra 12 generally includes a vertebral body, which extends on the anterior (i.e., front or chest) side of the vertebra 12. The vertebral body is generally in the shape of an oval disk. The vertebral body includes an exterior formed from compact cortical bone. The cortical bone encloses an interior volume of reticulated cancellous, or spongy, bone (also called medullary bone or trabecular bone). A "cushion," called an intervertebral disk, is located between the vertebral bodies. An opening, called the vertebral foramen, is located on the posterior (i.e., back) side of each vertebra 12. The spinal ganglion pass through the foramen. The spinal cord passes through the spinal canal. The vertebral arch surrounds the spinal canal. The pedicle of the vertebral arch adjoins the vertebral body. The spinous process extends from the posterior of the vertebral arch, as do the left and right transverse processes.

Figure 2:
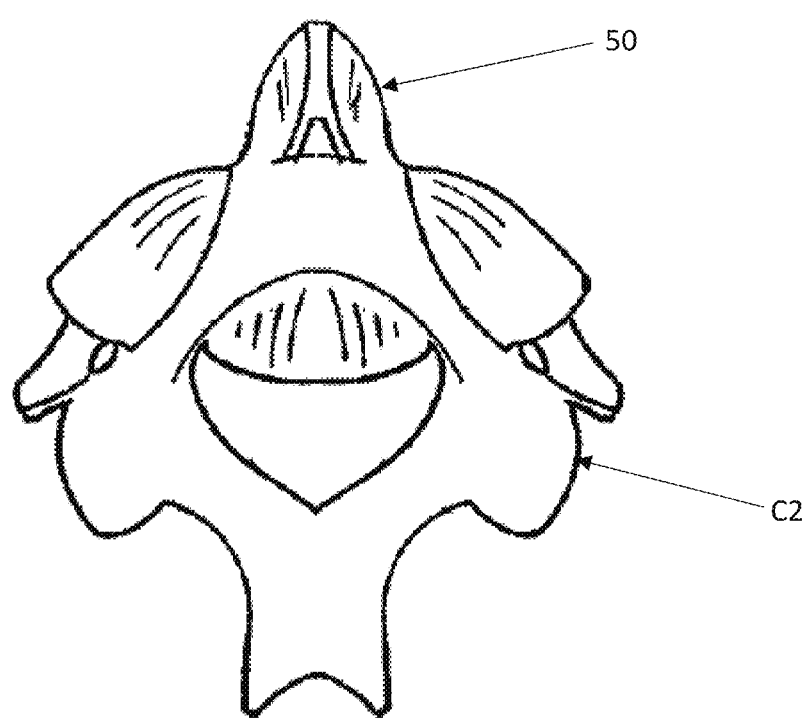
FIG. 2 depicts an exemplary second cervical vertebrae.

FIG. 2 depicts an exemplary second cervical vertebrae, referred to as "C2," which forms a pivot upon which the first cervical vertebra (C1—the atlas—which carries the head) rotates. A distinctive characteristic of the C2 vertebrae is the strong odontoid process 50 ("dens"—also referred to herein as "odontoid"), which rises perpendicularly from the upper surface of the body.

Figure 3:
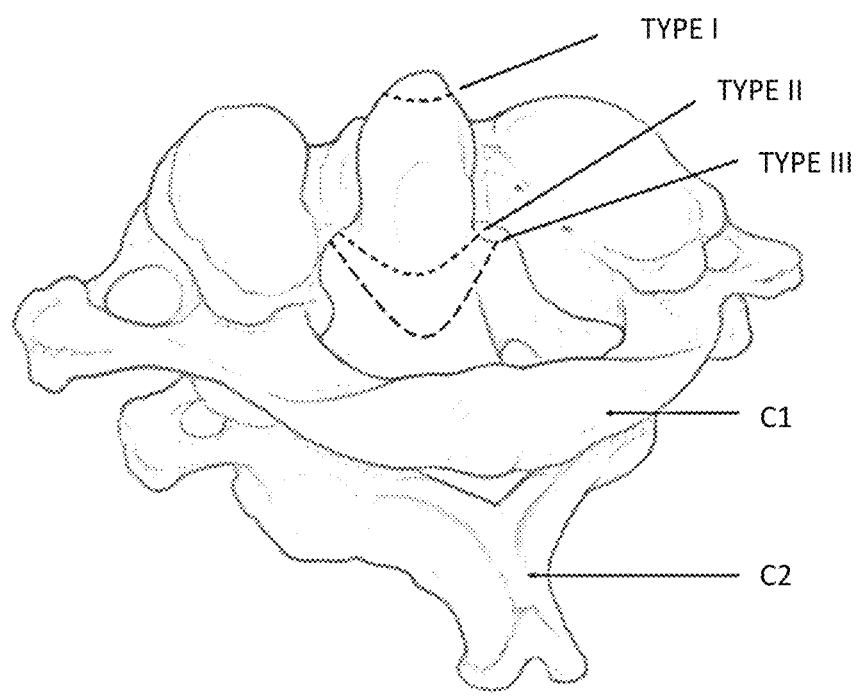
FIG. 3 depicts interlinked C1 and C2 vertebrae with various common types of odontoid fractures identified in dotted lines.

FIG. 3 depicts interlinked C1 and C2 vertebrae with various common types of odontoid fractures identified in dotted lines, including Type I, Type II and Type III odontoid fractures. In general, Type I fractures involve a small amount of bone at the tip of the odontoid process, and these fractures are often treated with traction and cervical collar immobilization (i.e., using halo/Minerva fixation), while Type II fractures are most successfully treated using fixation screws and/or plates. Type III fractures, which often involve a patient who has sustained multiple traumatic injuries, can be treated with traction and cervical collar immobilization, but are often most successfully treated with cervical fusion of the C1 and C2 levels.

A Type II odontoid fracture generally occurs at the base of the odontoid as it attaches to the body of C2. Options for treating type-2 odontoid fractures include halo stabilization as well as C1-C2 fusion or internal fixation, but halo stabilization is often poorly tolerated by patients with these fractures. Similarly, C1-C2 fusion is generally unpopular for these patients, as this type of surgery typically eliminates at least 50% of cervical rotation. In most current cases, therefore, anterior screw fixation with single or dual cannulated screws is the standard internal fixation technique—however such screw fixation often does not provide adequate stabilization of the fracture secondary to poor fixation in the C2 body, and also is less than optimal where the fracture fragment(s) does not possess adequate structural stability to accommodate screw-based fixation.

The various teachings of the present invention provide for securement and fixation for all varieties of odontoid fractures, including fractures involving unusually shaped fragments and/or a plurality of bone fragments. It will be apparent that the various components, tools and surgical techniques described herein can provide a number of attendant advantages, including the ability to fixate odontoid fractures not adequately addressed by conventional treatment techniques. Moreover, the various treatments described herein can, for various individuals, restore the load bearing capability of the odontoid region virtually immediately after surgery, which can greatly improve patient satisfaction and/or outcomes measures for the surgery as compared to traditional treatments.

In various embodiments, the disclosed devices, systems and methods can be used as a substitute for existing screw-based fixation techniques and implants for odontoid fracture surgery, including various surgical techniques, tools and related implants described herein. Various embodiments disclose a flexible tether based compressive fixation system, wherein a first anchor (which may comprise a relatively rigid, elongated portion or "bullet") is introduced across a fractured odontoid region, and the flexible tether is tensioned between the first anchor and a second anchor, whereby the fracture region is compressed and the odontoid fracture fragment(s) is desirably immobilized relative to the remaining C2 bone. Properly employed, the disclosed system can secure the fractured portion(s) of the odontoid to the native remainder of the vertebral bone structure, thereby fixating and/or "reinforcing" the fractured portion and facilitating continued normal function of the patient's anatomy and reduced recovery time. Moreover, the various system components further allow for minimally-invasive removal of the odontoid bullet and associated fixation components, in the event of further fracture, implant failure and/or healing of the fractured bone portion.

The present invention desirably provides minimally invasive, flexible fixation of the odontoid fragment, which in various embodiments may allow desirable micro-motion at the fracture point. In various embodiments, there may be no need for routine removal of the implant and its use should enable patients to ambulate at an earlier stage that with traditional cervical spine surgery.

Figure 4A:
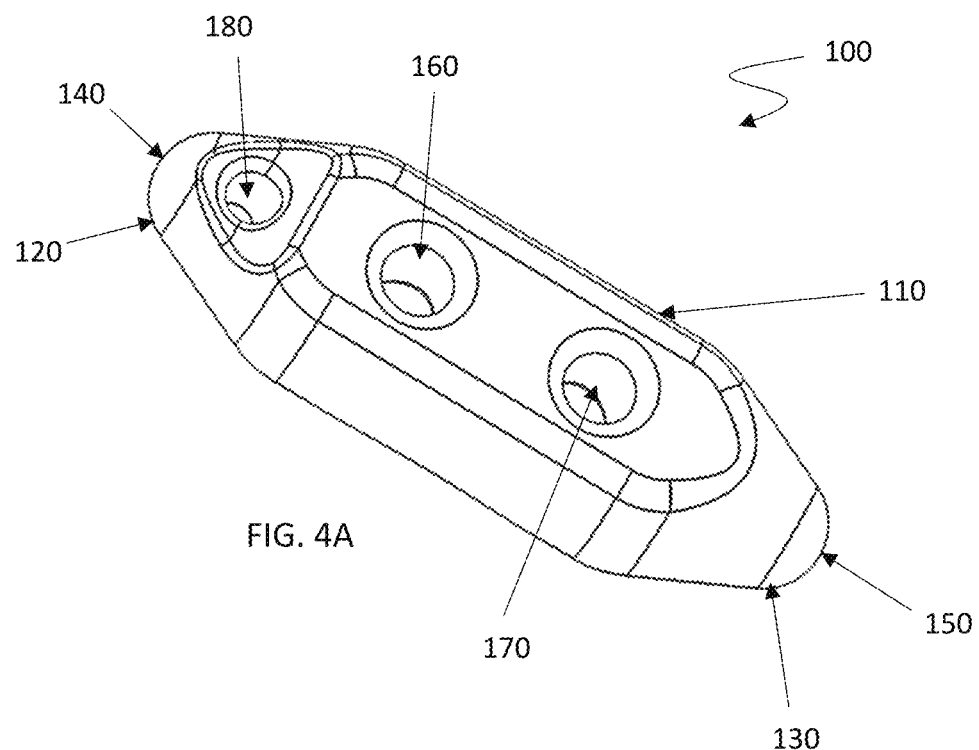
FIGS. 4A and 4B depict front and back perspective views of one exemplary embodiment of a bullet device.
Figure 4B:
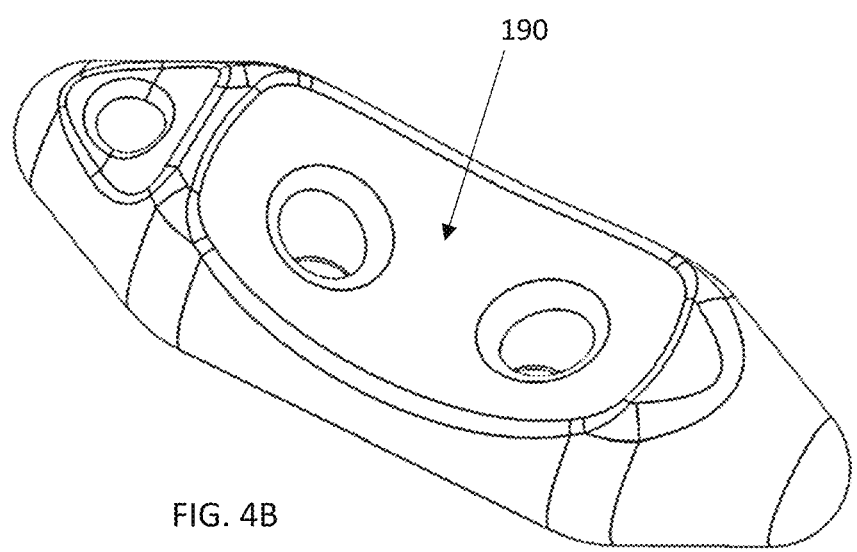
Figure 4C:
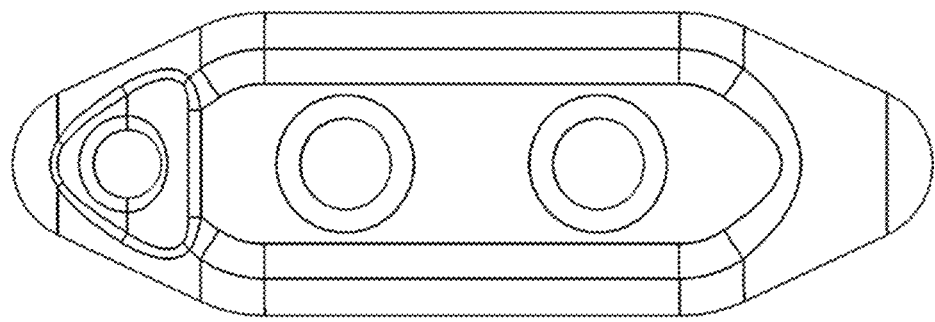
FIGS. 4C through 4H depict various plan views of the bullet device of FIGS. 4A and 4B.
Figure 4D:
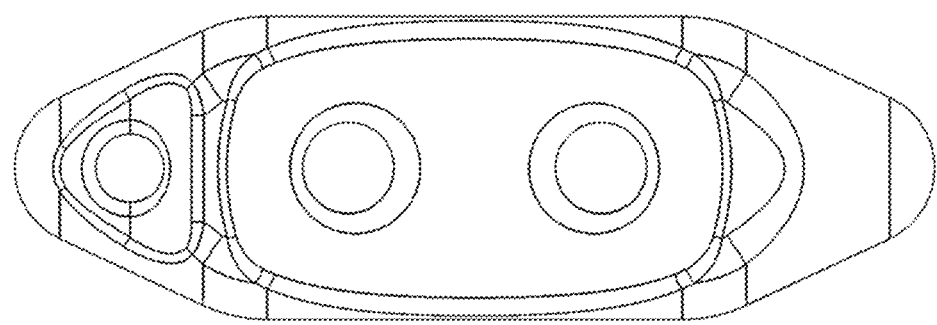
Figure 4E:
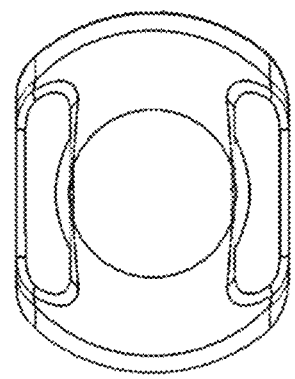
Figure 4F:
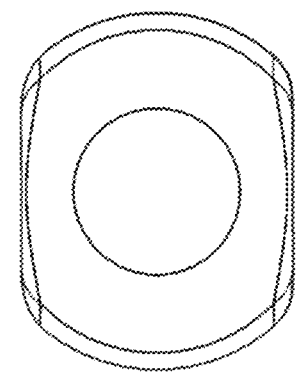
Figure 4G:
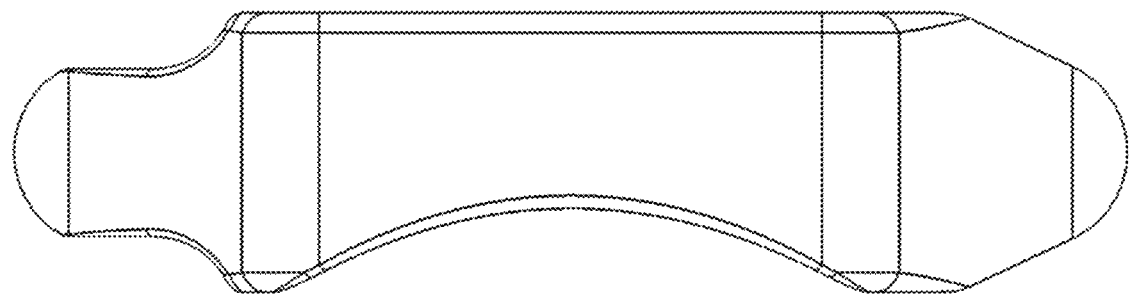
Figure 4H:
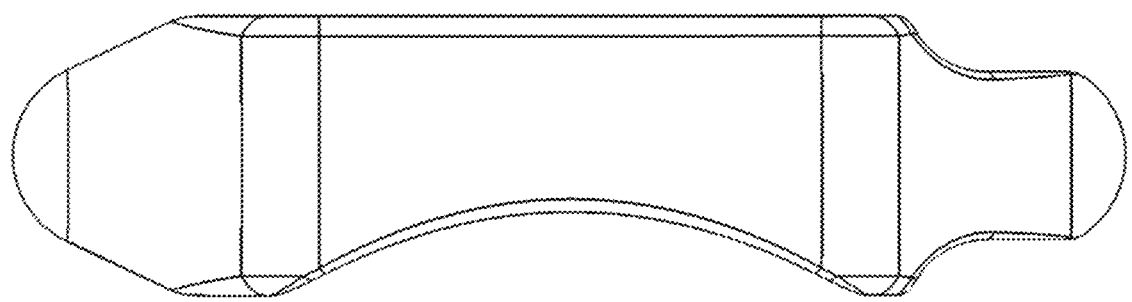

FIGS. 4A and 4B depict front and back perspective views of one exemplary embodiment of a bullet device 100 for use in conjunction with the various teachings provided herein. The bullet 100 includes an elongated, generally cylindrical body 110 with a proximal end 120 and a distal end 130. The proximal end 120 presents a gradually tapered profile, with the proximal end terminating in a generally blunt proximal tip 140. The distal end 130 similarly presents a gradually tapered profile, with the distal end terminating in a generally blunt distal tip 150. A plurality of fixation openings 160 and 170 are formed in the elongated body 110, through which a flexible fixation member (not shown) can extend for placement and tensioning of the construct. A recovery opening 180 is also formed in the elongated body near the proximal end 120. The recovery opening 180 desirably accommodates a flexible recovery member (not shown), which can be utilized to remove the bullet via the surgical path through the C2 body when implant removal is desired and/or warranted.

As best seen in FIG. 4B, the elongated body 110 also includes a central recessed region 190 extending beyond the fixation openings 160 and 170. While the central recessed region 190 is shown as a gently curved concave surface, it should be understood that other shapes, including shapes having greater curvatures and/or lesser curvatures (and/or three dimensional curvatures, if desired), as well as flat surfaces and/or angled surfaces, could be incorporated. Similarly, in alternative embodiments the central recessed region 190 could comprise a convex surface that presents to the underlying bony surface(s), and/or various combinations of concave, convex, flat and/or angled surfaces, if desired. FIGS. 4C through 4I depict various plan views of the device of FIGS. 4A and 4B.

Figure 5A:
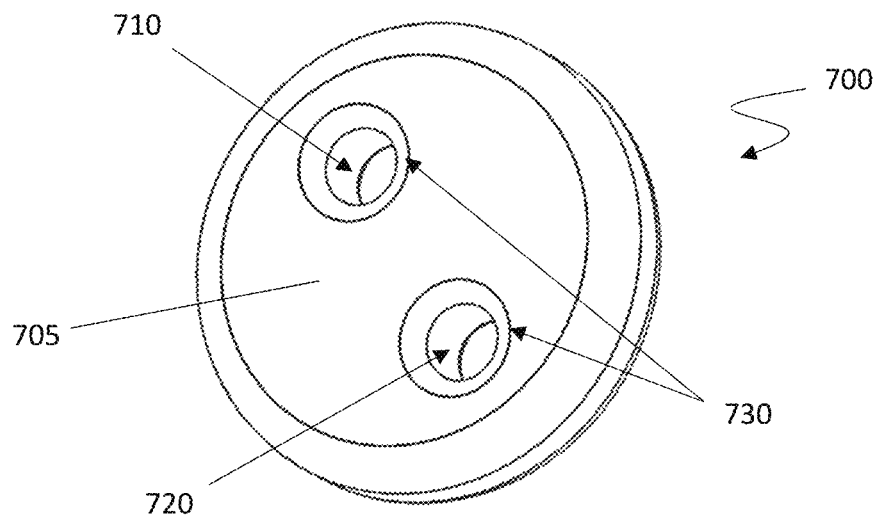
FIGS. 5A through 5C depict various views of one embodiment of a button device.
Figure 5B:
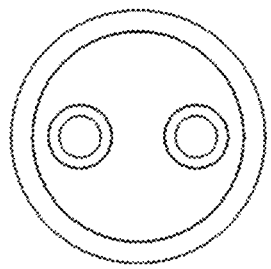
Figure 5C:
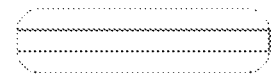

FIG. 5A depicts a perspective view of one embodiment of a button 700 for use in securing the odontoid fragment(s) in a desired position. The button 700 comprises a disc-shaped body 705, with one or more button openings 710 and 720 (in this embodiment, two holes) extending there through. Each of the button openings desirably incorporate rounded or tapered edges 730, which reduce the likelihood of damaging the flexible members (not shown) which will extend therein. FIGS. 5B and 5C depict front plan and side plans views thereof.

It should be understood that some or all of the openings in the bullets and/or buttons described herein could be countersunk or otherwise rounded or tapered so as to allow easier threading passage of the flexible members and to reduce the potential for severing and/or fatigue fracture of the flexible members under loading conditions.

In various embodiments, a rounded button (such as the embodiments shown herein) may have any suitable dimension (diameter and thickness), as well as any suitable number of openings (i.e., 1 or 2 or 3 or 4 or more). For example, a rounded button embodiment might have a diameter of about 5.5 mm and a thickness of about 1.27 mm. The centers of the apertures could be about 1.27 mm from the center of the button and the centers of the pair of apertures could lie substantially along an axis passing through the center of the button. The apertures of the rounded button can have any shape, including shapes where each aperture is desirably equidistant from the center of the rounded body. One preferred embodiment is an aperture, which is substantially round in plan-view. Another embodiment could be an egg-shaped or oval aperture.

Aspects of the invention further relate to methods for installing the bullet and associated bone fixation system components in a human patient. Initially, at least a portion of a cervical spine of an associated patient is exposed to reveal the vertebral body to be repaired. Access to the vertebral body can be accomplished from many different directions, depending upon the targeted location within the vertebral body, the intervening anatomy, and the desired complexity of the procedure. For example, access can also be obtained through a pedicle (transpedicular), outside of a pedicle (extrapedicular), along either side of the vertebral body (posterolateral), laterally or anteriorly. In addition, surgical approaches could be used with a closed, minimally invasive procedure or with an open procedure.

In at least one exemplary surgical procedure, general endotracheal anesthesia can be used and the patient may be placed in the supine position with the patient's head secured by tongs or some other device or mechanism to allow reduction of the fracture. The head may be secured on a radiolucent operating table with the mouth held open with a radiolucent bite block, with single and/or biplane fluoroscopy used throughout the operation to guide the placement and motion of surgical tools, any desired reduction of the fracture and/or for placement of one or more components of the cervical fixation system. The patient's head can be positioned under lateral fluoroscopic guidance so that the neck could be extended to permit a trajectory for proper passage creation and/or insertion of the device.

Figure 21:
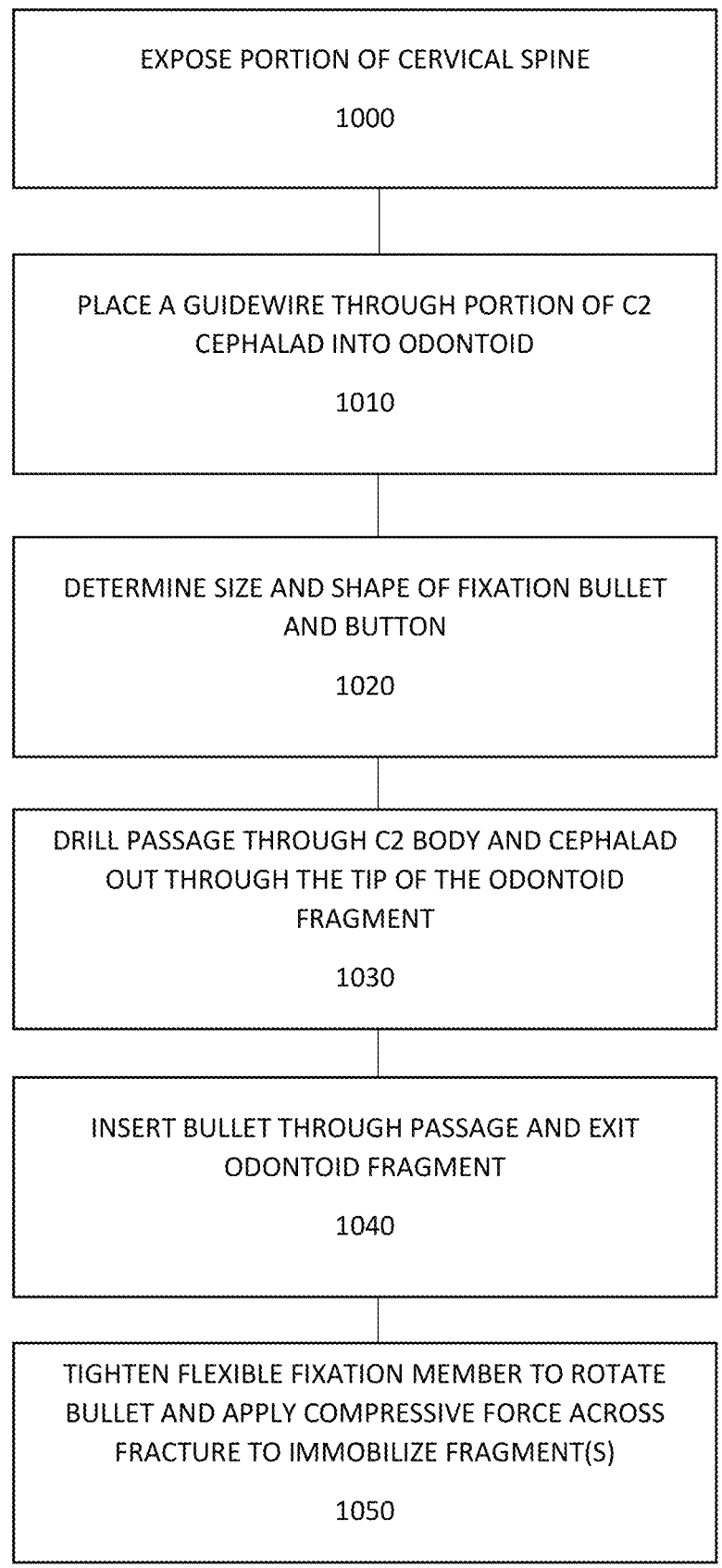
FIG. 21 depicts a flowchart of exemplary surgical steps on one embodiment of an odontoid fixation procedure.

In one exemplary embodiment (see FIG. 21), an anterior exposure to the cervical spine 1000 could be performed. For example, a left or right incision, depending on the surgeon's preference, is made longitudinally, inferior to the body of C2. Such an incision would desirably allow optimal angulation of any guide wires, drills and/or the bullet device, tension member(s), recovery member(s) and associated fastening devices. If desired, the midline antero-inferior aspect of the C2 body can be identified, such as by cutting a gutter into the anterior body of C3 and the C2-C3 disk to provide adequate visualization of the antero-inferior endplate of C2.

Figure 6A:
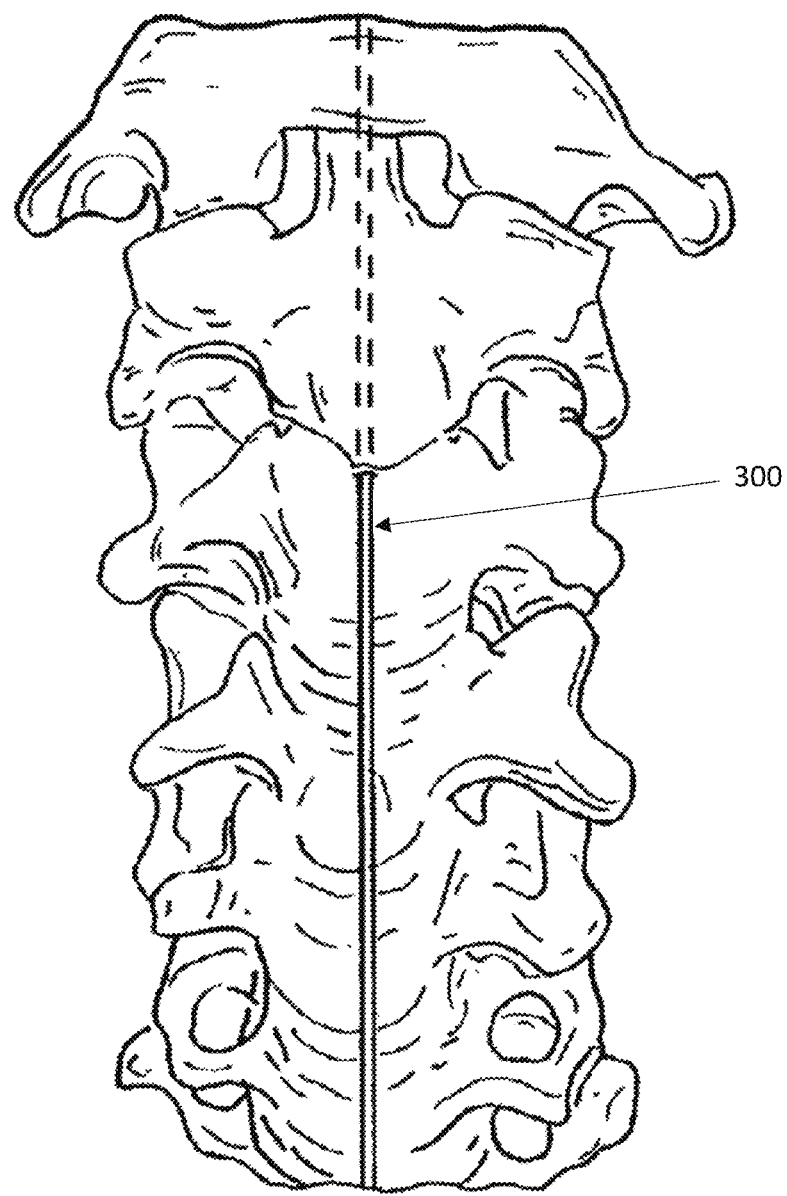
FIGS. 6A and 6B depict a partial spinal column, depicting one exemplary embodiment of a placement of a guide wire through a portion of a C2 cephalad body into an odontoid fragment.
Figure 6B:
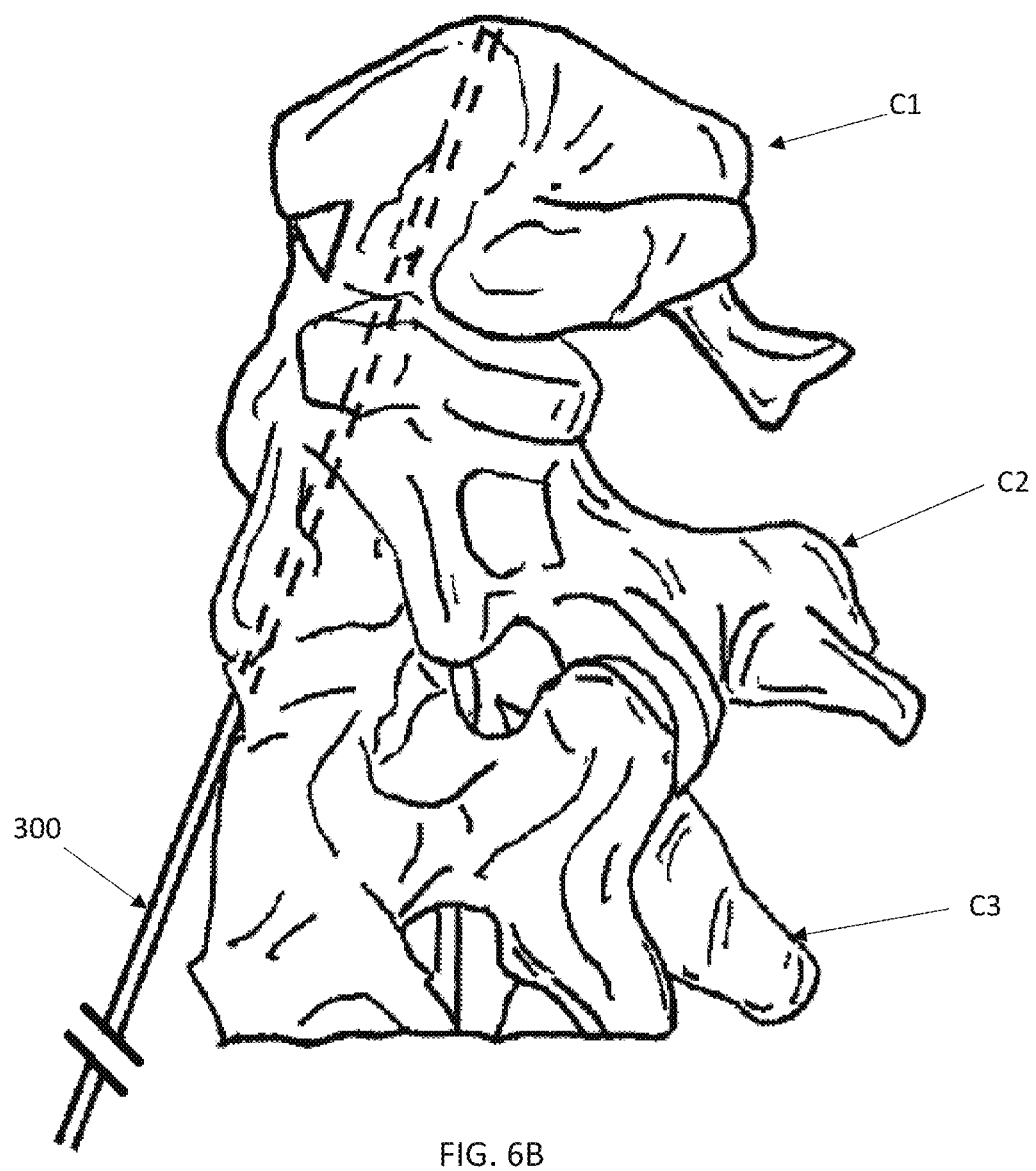

As best shown in FIGS. 6A and 6B, a guide wire 300 is placed through a portion of a C2 cephalad body into the odontoid 1010. If desired, a drill guide or other similar tool could be placed on the antero-inferior lip of C2 in the midline (or other position as desired by the surgeon). Generally, a C-arm guide or other such non-invasive imaging device may be used for precise placement of the guide wire into and through the odontoid and/or the avoidance of sensitive anatomy such as the spinal cord. For example, under fluoroscopic control, a 1.2 mm diameter Kirshchner wire (K wire) could be positioned on the anterior aspect of the inferior endplate of C2. The K wire could be advanced manually or with aid of a pneumatic drill so that the tip engages the cortex of the tip of the dens. If desired, one or more additional guide wires may be placed in the odontoid and/or through other anatomy in order to allow for de-rotation or adjusting of the position of the odontoid fragment(s). In various instances, the second guide wire or other surgical tools may be used to allow a surgeon to adjust alignment of the odontoid to an anatomically desired position prior to, during and/or after placement of the bullet and associated structures.

At some point in the surgical procedure (or preoperatively, if perioperative imaging has been used), a size, shape and/or length determination could be made to determine an appropriate size and/or shape of the bullet and/or button to desirably secure the odontoid fragment(s) to the C2 body 1020. This selection could include identification of the bony anatomy proximate to the exit point of the passage out of the odontoid fragment, which might influence the physician's choice of bullet size, concavity, curvature and/or angulation. In various embodiments, a depth gauge or similar device could be placed over the guide wire 300, or the characteristics of the fixation device components may be determined in a variety of ways (e.g., X-rays, CT scans, measuring without the guide wire, etc.) preoperatively and/or during the surgical procedure.

Figure 7A:
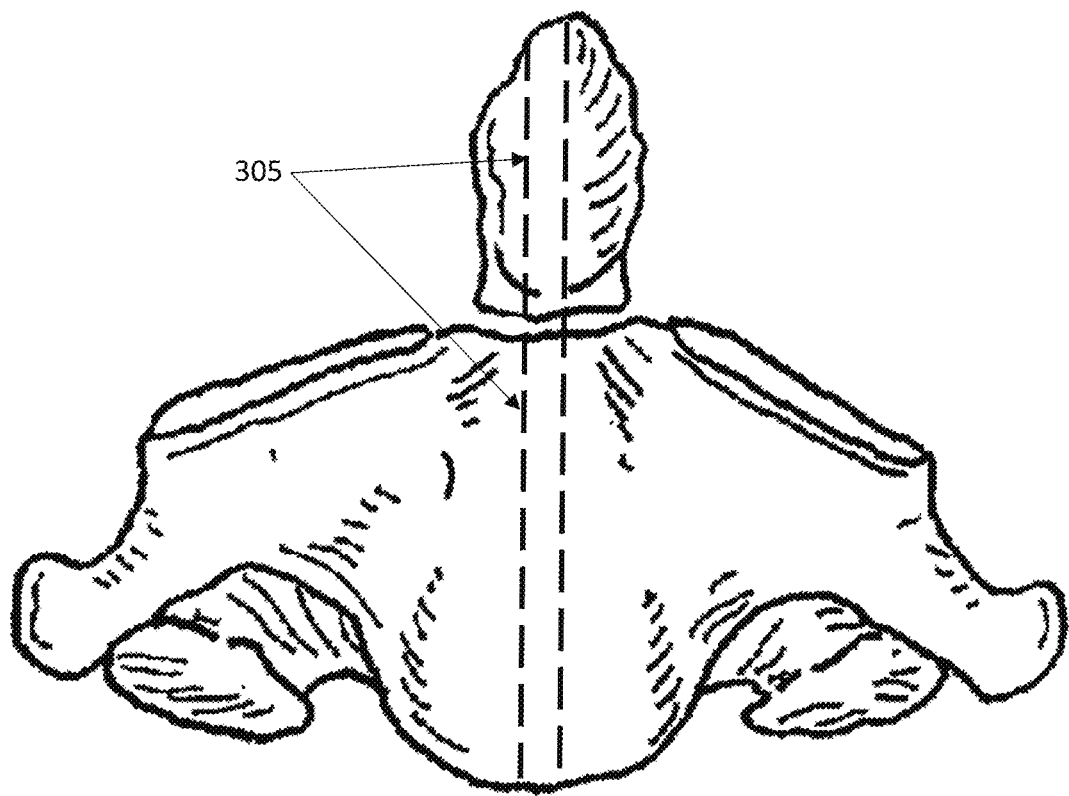
FIGS. 7A and 7B depict a partial spinal column, depicting one exemplary embodiment of a passage formed through a portion of a C2 cephalad body and odontoid fragment.
Figure 7B:
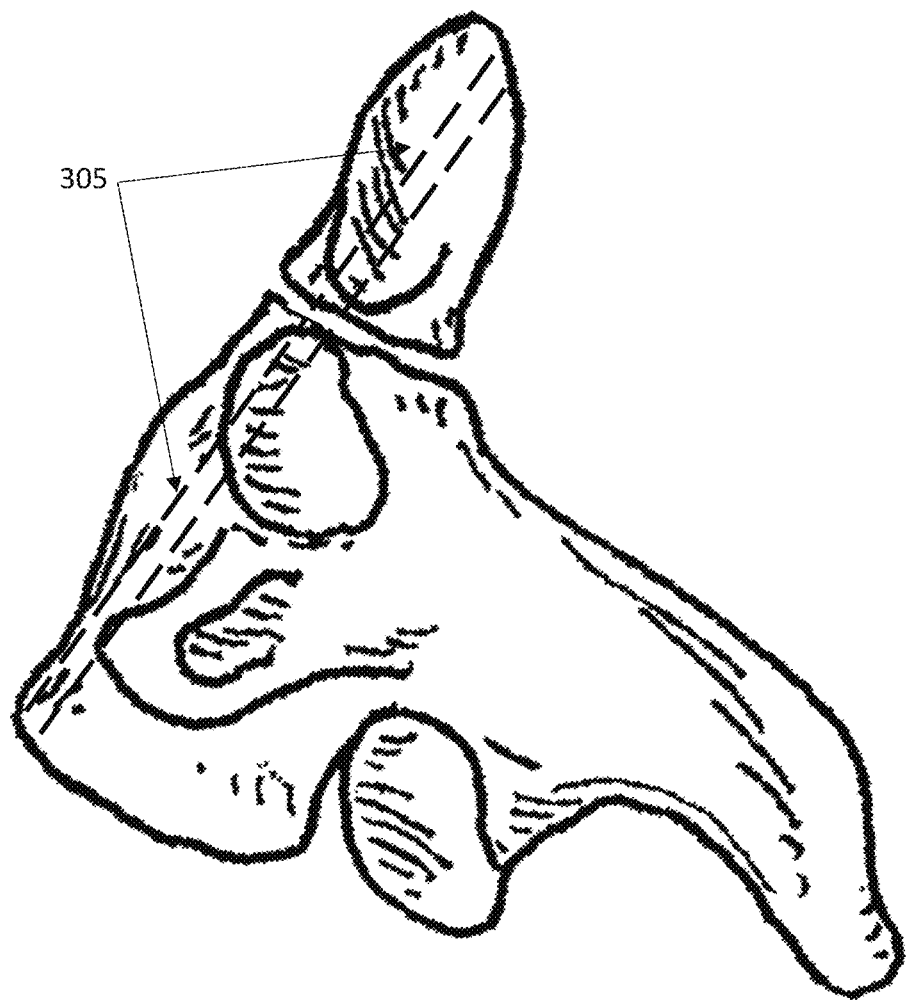

Desirably, a hole or passage can be drilled in a caudal to cephalad direction through the C2 body and out of the tip of the odontoid 1030, which may include the use of a cannulated drill following the guide wire 300, creating a passage 305 (as shown in FIGS. 7A and 7B). Real time bi-planar fluoroscopy could be used (if desired) to monitor progress of the drill until the drill bit just passes through the odontoid tip. In one embodiment, the hole may be approximately 2.5 to 4.0 mm, with the hole desirably large enough in diameter to accommodate passage of an appropriately sized and shaped bullet. One of ordinary skill in the art will appreciate that the disclosed diameter is exemplary in nature and any appropriate diameter selected by a surgeon should be within the scope of the present disclosure. Desirably, the depth of drilling will match a length determination (of the C2 body and odontoid fragment) from the previously described measuring step, with the passage passing through the odontoid fragment.

Figure 8B:
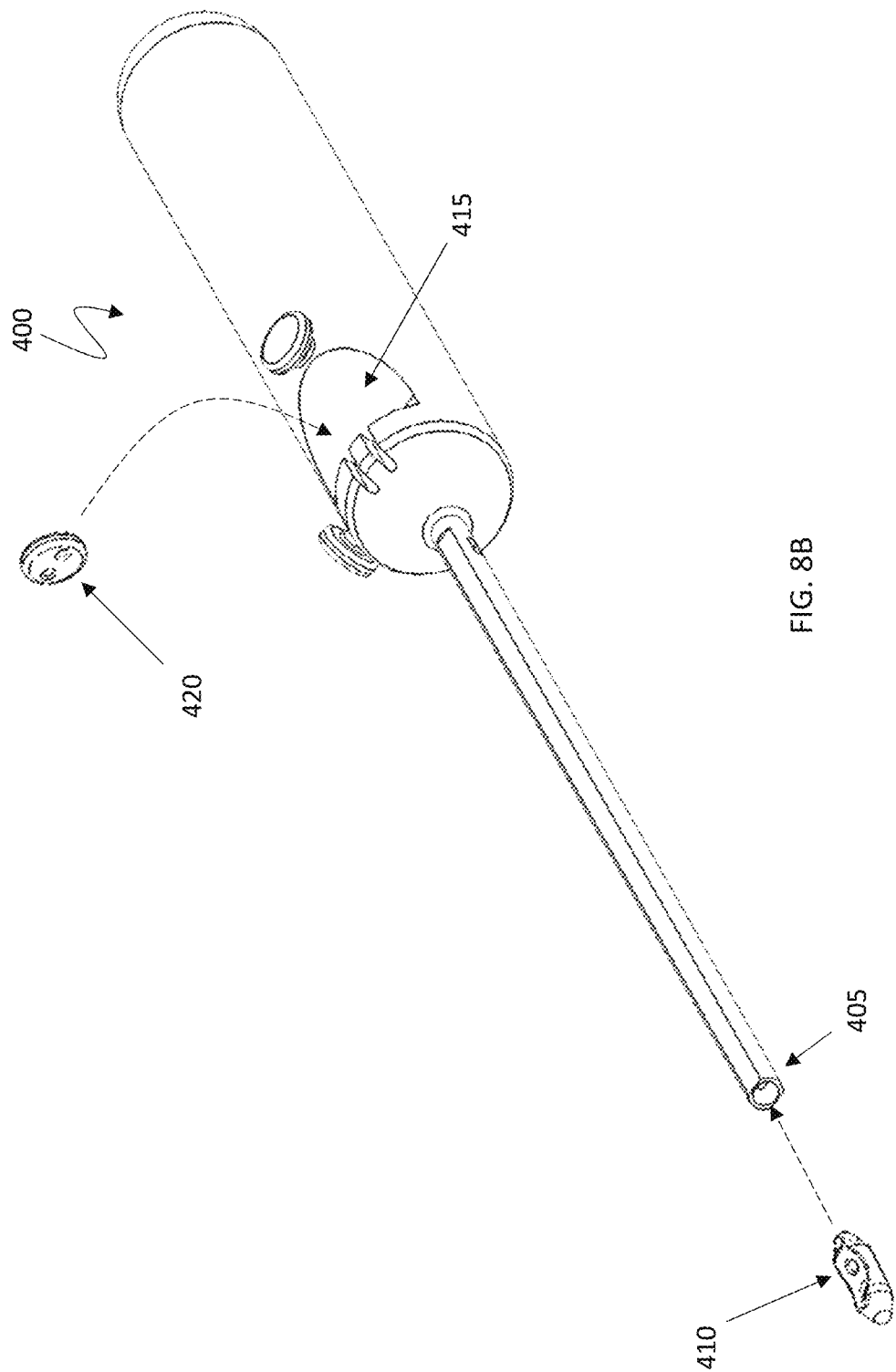
Figure 8C:
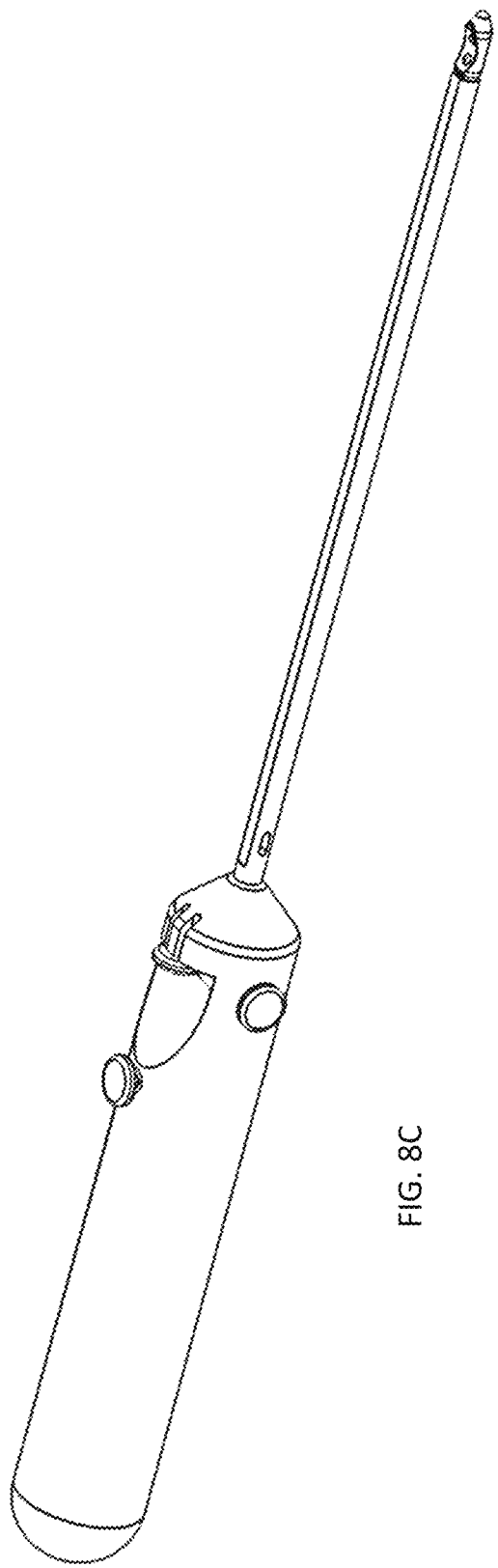

Once drilling of the passage is complete, the physician can select an insertion tool 400, which can desirably be pre-loaded with appropriate bullet 410 at a distal end 405, a button 420 in a handle receiver portion 415, flexible fixation members 430 extending between the bullet and button, and a flexible recovery member 440 extending down through a lumen 460 in the insertion tool (see FIGS. 8A through 8C). Desirably, the flexible recovery member 440 can be tensioned to draw the bullet into a corresponding receiving portion of the distal tip, aligning the longitudinal axis of the bullet with the insertion tool and holding these components together in a relatively rigid fashion. In various embodiments, the inner surface of the receiving portion can have a shape that matches and/or compliments the outer shape of the proximal end 120 of the bullet, which desirably engages with and secures the bullet so as to allow the bullet to be rotated while advancing and/or withdrawing the insertion tool into and/or out of the passage (see FIG. 8B), while in other alternative embodiments the inner surface of the receiving portion could have a more regular or frusto-conical shape.

In various embodiments, the bullet could have one or more high strength flexible members attached thereto, including suture tape (preferably a high strength tape formed of ultrahigh molecular weight polyethylene—sold under the brand name FiberTape® by Arthrex, Inc. of Naples, Fla.) or pull-through suture strand (preferably a high strength suture such as #2 FiberWire® sold by Arthrex, Inc. of Naples, Fla.), with the FiberTape or FiberWire sutures preattached to the device when loaded onto an insertion tool. One larger suture could comprise a flexible fixation band, which could be weaved through the center of the device and utilized as the main tension band between the bullet and the button or base anchor. A second smaller suture could comprise a removal or revision band that allows the bullet to easily be removed if necessary during or after the surgical procedure.

In use, the physician can insert the distal end 405 of the insertion tool and attached bullet 410 through the passage formed in the C2 body and the odontoid fragment. As previously noted, the relatively rigid engagement between the bullet and the insertion tool desirably allows the bullet and attached insertion tool to be advanced/withdrawn and rotated during advancement and/or retraction, which desirably reduces the forces necessary to insert/withdraw the bullet. As the bullet advances out of a distal end of the passage in the odontoid fragment 1040, it may be desirous to reduce and/or release the tension on the flexible recovery member 440, which can allow the bullet to move and/or flex relative to the tip of the insertion tool. Once the bullet 410 begins to leave the passage (or where the bullet has been fully advanced out of the passage), the flexible fixation wires can be tensioned to some degree, which will tend to rotate or flip the bullet 410 within the soft tissue space so as to present an enlarged profile to the bone passage and/or the surface of the odontoid fragment 1050. Further tension on the flexible fixation wires will desirably draw the bullet into intimate contact with the odontoid fragment, and desirably some portion of the fragment surface can desirably enter and/or engage with at least a portion of the concave surface of the central recessed region 190 (see FIGS. 9A and 9B), such that when the flexible fixation wires are fully tensioned to a desired level, the bullet will induce the fragment to engage with the C2 bone, desirably causing a compressive loading force across the fractured bone region.

One significant advantage of the present system over prior art systems is the ability of the present system components to accommodate unstable bone fragments and/or fragments that are unable to withstand the internal "hoop stresses" typically induced by screw-based fixation systems. In prior art fixation systems, the odontoid fragment desirably has sufficient size and structural integrity to accommodate the threads of the fixation screw, which "bite" into the inner bone surface and induce an outward-acting circumferential force on the fragment (i.e., the "hoop" stresses). In addition, prior art systems require strong threaded fixation into the odontoid fragment, which typically requires larger threads to be screwed into the fragment—again requiring a larger fragment to accommodate these needs. Moreover, screw-based fixation of odontoid fragments is contraindicated where there are fractures into the body of C2 (which do not allow firm screw purchase) or where oblique odontoid fractures exist that are steeply angled anteriorly.

In contrast, the present system does not rely on the structural integrity of the odontoid fragment and/or its ability to withstand drilling combined with screw-based fixation to maintain the fragment in a desired position. Rather the disclosed systems can be use with all manner of passages, including partially formed passages and/or "grooves" formed into an odontoid fragment, if desired. Moreover, the present systems could be used with surgical tunnels having non-uniform shapes and/or axes (i.e., "bent" or curved tunnels, which could include circular and/or non-circular cross sections).

Figure 9A:
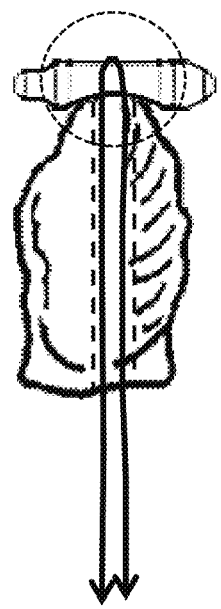
FIGS. 9A and 9B depict views of one embodiment of a flexible fixation member pulling an odontoid bullet into contact with a bone fragment.
Figure 9B:
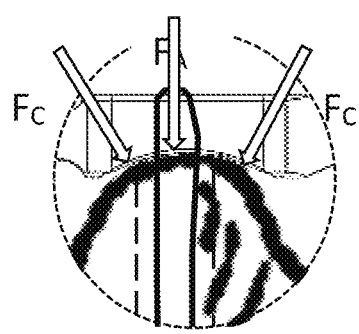

When the flexible fixation member of the present embodiment is tensioned, the member desirably pulls the bullet downward onto the bone fragment, and the concave curvature of the bullet can induce both an axial compressive force $F_A$ on the fragment (tending to push the fragment downward into the C2 body) and a radial compressive force $F_C$ induced by the curved surfaces (tending to push the sides of the fragment together), which tends to hold the fragment together rather than push it apart (see FIGS. 9A and 9B). The present system desirably provides compressive loading to the top of the odontoid (along with radial inward forces induce by the bullet curvature in contact with the bone), and the tension member pulls the odontoid into the remaining vertebral bone, thereby creating an extremely strong bond between the fragment and the bone, and allowing immediate and/or expedited loading of the fragment by the patient with significantly reduced recovery times.

Moreover, depending upon the selected bullet size and amount of curvature, a single bullet could potentially be utilized to secure more than one odontoid fragments, or could be utilized to treat one or more odontoid fragments of a size, shape and/or integrity that cannot be fixated using current screw-based techniques. For example, the curved inner surface of the button can provide varying amounts of lateral compression to the fragment(s), which may assist with the control and/or reduction of multi-piece fragments of the odontoid. In addition, in embodiments where the anchoring devices are positioned external to the bony anatomy, the compressive anchor loading occurs primarily on the outer cortex and/or cortical bone (which is generally considered the stronger bone type) as compared to the relatively weaker internal cancellous bone structures primarily relied upon by screw-based fixation methods.

In various embodiments, the odontoid bullet could be anchored via virtually any angle and/or configuration of tunnel passing in and/or through C2 (including minimally-invasive approaches and techniques and/or off-axis approaches), which allows very secure fixation of the odontoid to C2, yet allows for significant surgical freedom and approach selection.

Figure 8D:
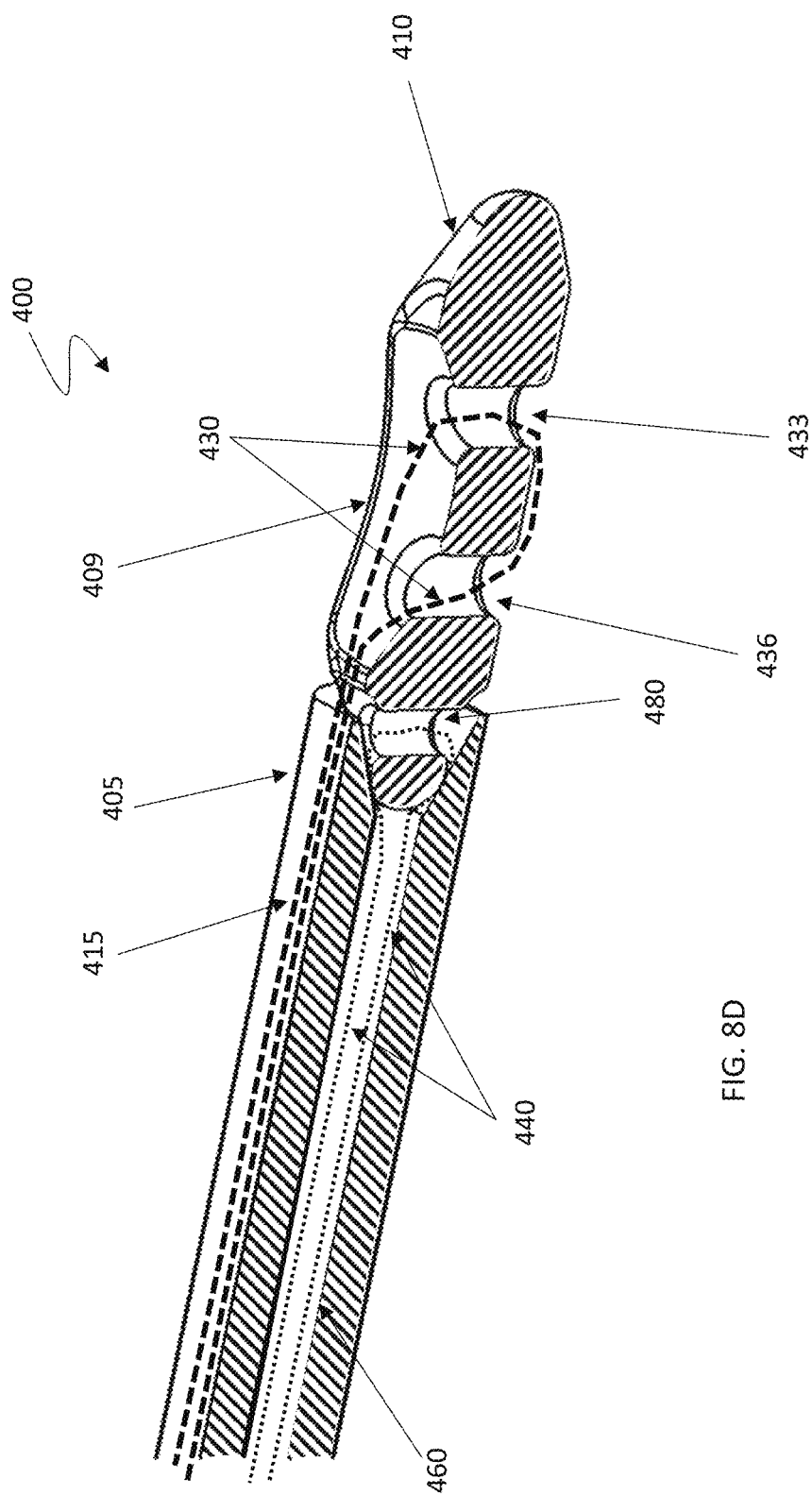
FIG. 8D depicts a partial cross-sectional view of the insertion tool and bullet of FIG. 8C.
Figure 8E:
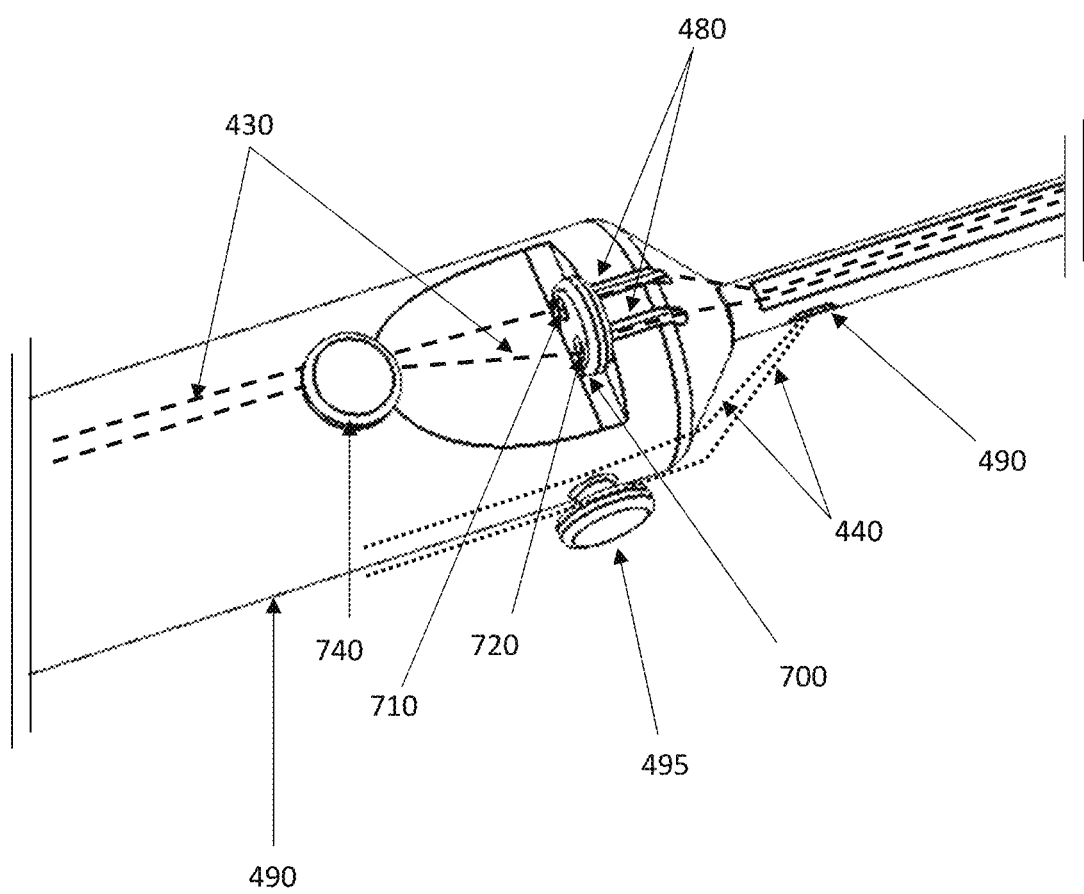
FIG. 8E depicts a partial perspective view of the handle and button of FIG. 8C including flexible members.

FIG. 8D depicts a partial cross-sectional view of the distal tip 405 of one embodiment of an insertion device 400, with an associated bullet 410 loaded therein. The flexible fixation member 430 is threaded through the fixation openings 433 and 436, with the fixation member 430 extending outward of the central recessed region 409 and extending downward along an outer surface 415 of the insertion device 400. A flexible recovery member 440 extends upwards through a lumen 460 within the insertion device 400, loops through a recovery opening 480 and extends back downward in the lumen 460. As best seen in FIG. 8E, the flexible fixation member 430 travels along the outside surface of the insertion device 400 and passes up into grooves 480 formed in a handle 490. The fixation member 430 passes through button openings 710 and 720 in a securement button 700 and then passes proximate to a fixation member knob 740 extending outward from the handle. The recovery member 440, which extends within the lumen 460 in the insertion device (as previously described), exits the lumen 460 through a shaft opening 490, with the recovery member 440 extending along the handle 490 and passing proximate to a recovery member knob 495 extending outward from the handle 490.

In various alternative embodiments, the bullet and button could be secured or pre-threaded together by the flexible fixation member, which could be double looped through the openings in the bullet and button in a known manner. In other alternative embodiments, the bullet and/or button could incorporate one-way or locking fasteners in one or more openings.

Figure 20A:
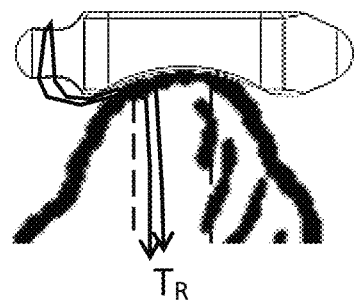
FIG. 20A depicts a partial plan view of an odontoid fragment and an associated bullet device.
Figure 20B:
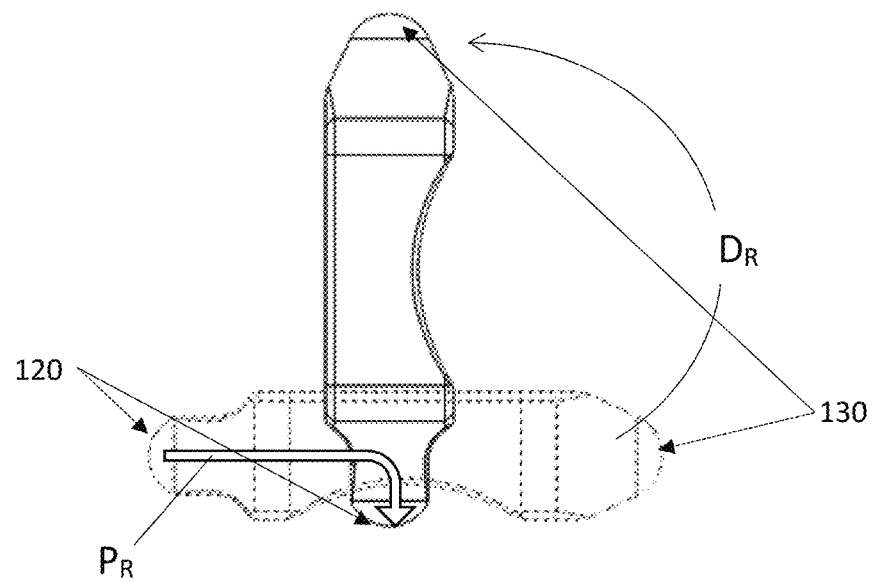
FIG. 20B depicts one exemplary motion path of a bullet during a bullet recovery procedure.

Another significant improvement of various embodiments over the prior art is the inclusion of one or more recovery openings formed in the odontoid bullet which, in the event of further bone fracture, implant failure and/or healing of the fractured bone portion, facilitates the less-invasive and/or minimally-invasive removal of the bullet component (and related fixation components) from the patient. The positioning and placement of the recovery opening, in conjunction with the attached recovery member, desirably allows the odontoid bullet to be removed from the C2 body via the existing surgical passage through the bone. As best shown in FIGS. 20A and 20B, a tension force $T_R$ on the recovery member (where the previously described fixation members have been de-tensioned and/or severed) will tend to pull the proximal end 120 of the bullet towards the surgical passage (along path PR), while also rotating the distal end 130 of the bullet away from the passage (along path DR). Desirably, sufficient tension force on the recovery member will ultimately align the bullet with the surgical passage, thereby allowing the bullet to be drawn down the existing passage with little or no disruption to surrounding tissues. Once removal of the bullet is completed, the surgical passage may be utilized for additional procedures (i.e., including placement of a replacement implant such as a new bullet and/or a conventional screw-based fixation, if desired) if desired, or the passage may be filled with bone graft material or other filing material (i.e., bone cement).

In one exemplary embodiment, the recovery member can extend through the surgical tunnel after the implant is installed, with some portion of the recovery member attached to a caudal portion of the tunnel (i.e., to a caudad button or other feature), with some amount of "slack" being desirably provided in the recovery member. If removal of the bullet is desired, the main tension member (i.e., the fixation member extending through one or more of the fixation openings) can be severed or loosened, and the recovery member desirably tensioned, which can cause the bullet to relax or "lift off" from the odontoid fragment to some degree and/or otherwise permit pulling on the recovery member to realign the bullet with the surgical tunnel, with the bullet ultimately pulled through the tunnel for removal from the patient.

In various embodiments, the described odontoid implant components and/or various surgical tools described herein could be provided in a kit containing multiple sizes and/or shapes of odontoid bullets and/or buttons for selection by the surgeon. In various alternative embodiments, a series of different sized and/or shaped bullets could be provided in kit form, with the surgeon using a properly sized and/or shaped bullet as the cephalad implant (i.e., at the upper end of the surgical "tunnel"), with larger and/or other sized/shaped bullets used for a caudad implant (i.e., at the lower end of the surgical "tunnel"). Desirably, the kit may allow the surgeon to place two or more odontoid bullets and/or buttons in discreet locations that may require different sizes and/or shapes.

In one exemplary embodiment, a kit containing a series of different size bullets could be provided for a surgical procedure, including one or more of the following size combinations:

| BULLET | WIDTH (mm) | LENGTH (mm) | SEE FIG. |
| --- | --- | --- | --- |
| 3 × 8 | 3 | 8 | 11A and 11B |
| 3 × 10 | 3 | 10 | 12A and 12B |
| 3 × 12 | 3 | 12 | 13A and 13B |
| 4 × 8 | 4 | 8 | 14A and 14B |
| 4 × 10 | 4 | 10 | 15A and 15B |
| 4 × 12 | 4 | 12 | 16A and 16B |
| 5 × 8 | 5 | 8 | 17A and 17B |
| 5 × 10 | 5 | 10 | 18A and 18B |
| 5 × 12 | 5 | 12 | 19A and 19B |

In various embodiments, the curved inner surface of the bullet (or other relevant features of the implant such as the length, diameter, number and placement of fixation or recovery holes, etc.) could include patient specific features, including bullet surface features designed to match or approximate the surface of the odontoid fragment, which may include use of non-invasive imaging to create an inner surface that matches or substantially matches the outer surface of the odontoid fragment (including the incorporation of three-dimensional and/or spherical bullet surface features, if desired). If desired, various manufacturing methods, including Computer Aided Design (CAD) and 3-D printing techniques can be utilized to design and/or manufacture a desired odontoid button using non-invasive imaging data, such as MRI and/or CT scans.

For various medical applications in the spine or for other bony anatomy, for example, the rounded or curved surfaces may be configured to mimic the contour of an underlying bony surface to which the device is attached and/or adjacent to, or the surface may include features that can prepare the underlying bony surface (i.e., roughened surfaces) and/or include surface features that can osseo-integrate with the bone surface, if desired.

Figure 10A:
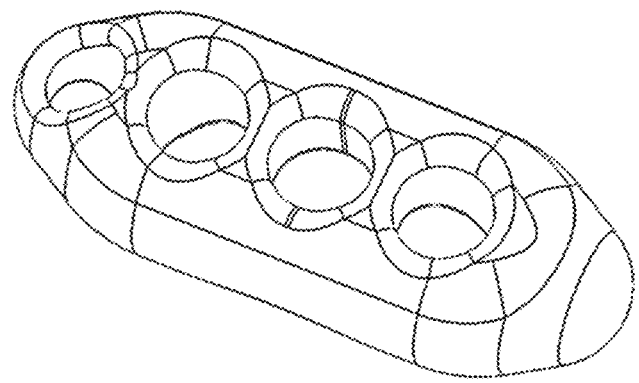
FIGS. 10A through 10F depict various views of one alternative embodiment of a bullet.
Figure 10B:
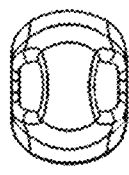
Figure 10C:
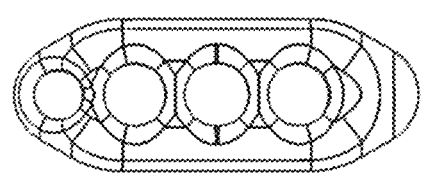
Figure 10D:
Figure 10E:
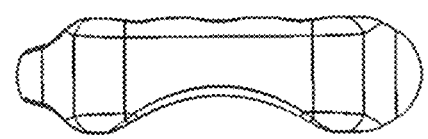
Figure 10F:
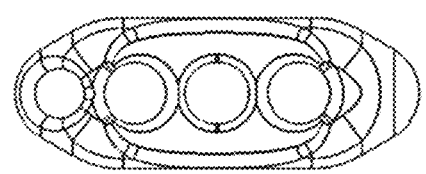
Figure 11A:
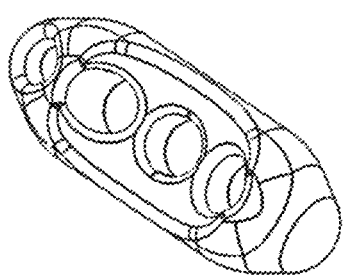
FIGS. 11A and 11B depict views of another alternative embodiment of a bullet.
Figure 11B:
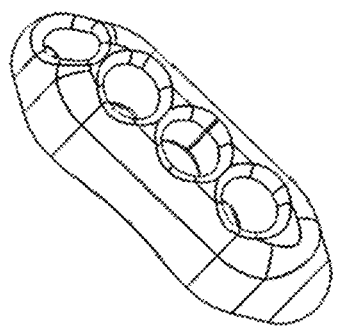
Figure 12A:
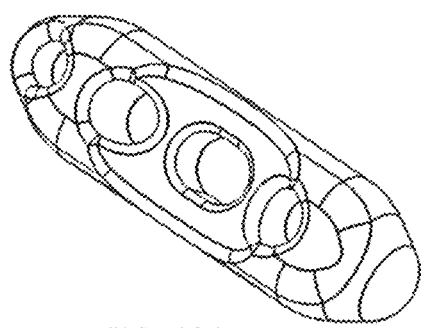
FIGS. 12A and 12B depict views of another alternative embodiment of a bullet.
Figure 12B:
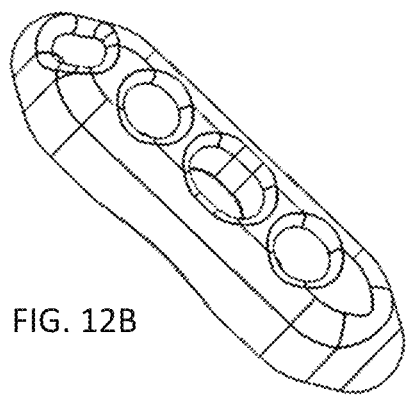
Figure 13A:
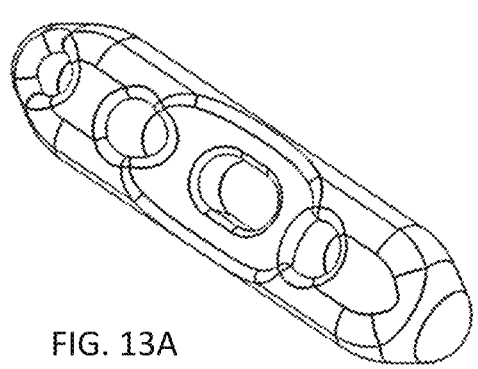
FIGS. 13A and 13B depict views of another alternative embodiment of a bullet.
Figure 13B:
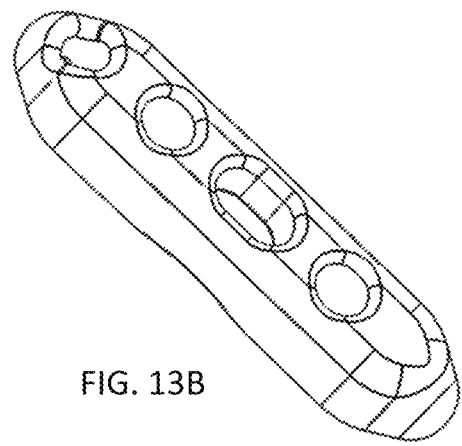
Figure 14A:
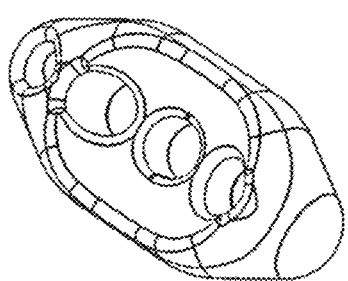
FIGS. 14A and 14B depict views of another alternative embodiment of a bullet.
Figure 14B:
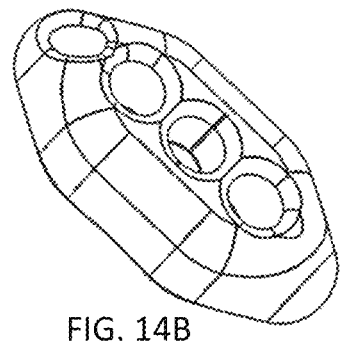
Figure 15A:
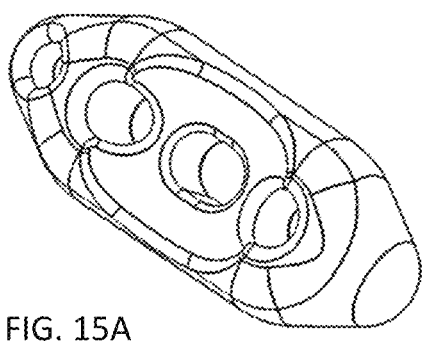
FIGS. 15A and 15B depict views of another alternative embodiment of a bullet.
Figure 15B:
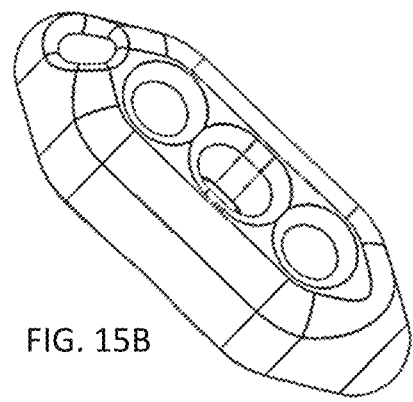
Figure 16A:
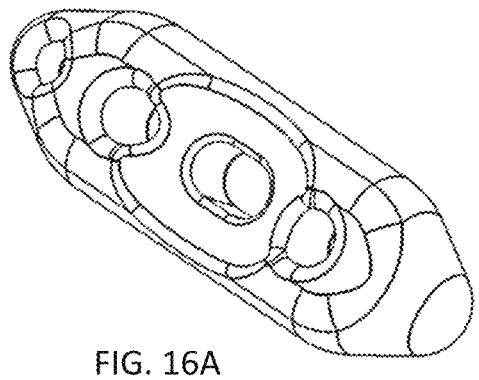
FIGS. 16A and 16B depict views of another alternative embodiment of a bullet.
Figure 16B:
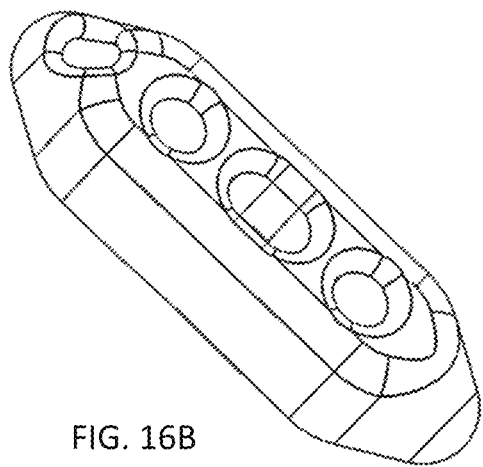
Figure 17A:
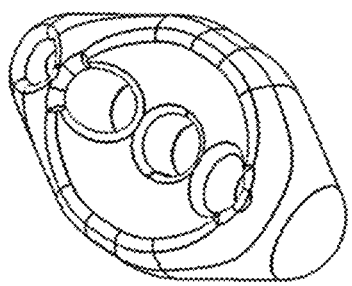
FIGS. 17A and 17B depict views of another alternative embodiment of a bullet.
Figure 17B:
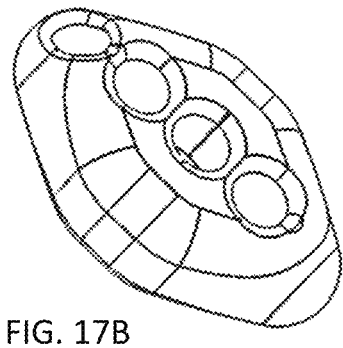
Figure 18A:
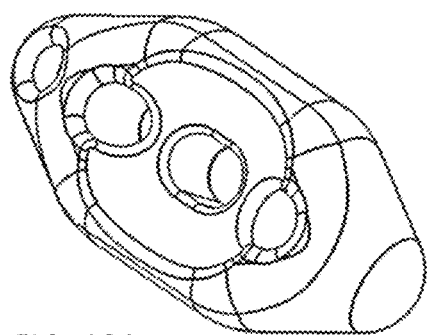
FIGS. 18A and 18B depict views of another alternative embodiment of a bullet.
Figure 18B:
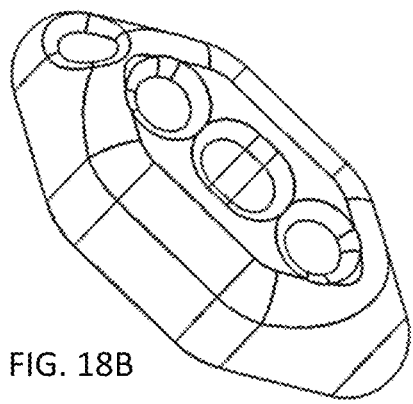
Figure 19A:
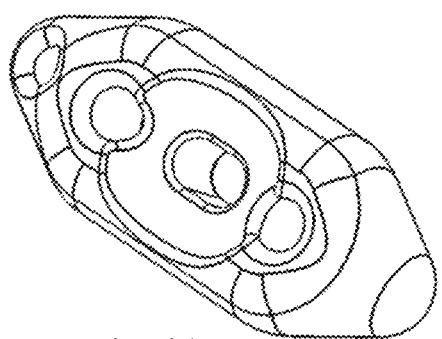
FIGS. 19A and 19B depict views of another alternative embodiment of a bullet.
Figure 19B:
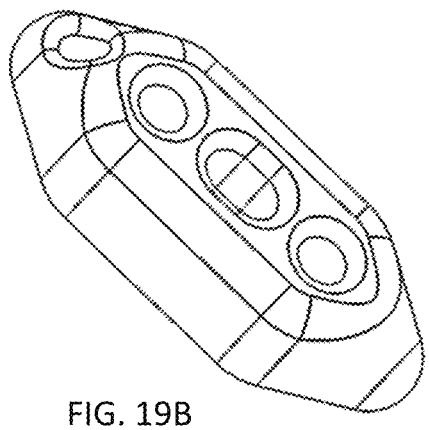

In at least one alternative embodiment, the various fixation components described herein could be used in conjunction with screw-based fixation devices for the treatment of odontoid fractures. For example, the odontoid bullet shown in FIG. 10A could include a central fixation opening that incorporated internally threaded features (not shown). Such an embodiment could allow for placement of the bullet proximate to the odontoid fragment (in a similar manner as previously described) using a tensioned flexible fixation member, but with the added step of allowing a fixation screw to be inserted through the surgical passage and threaded into the central fixation opening of the bullet, if desired.

In various alternative embodiments, the bullet and button components could incorporate one or more bony ingrowth surfaces, which could allow natural healing and permanent fixation of these components to the bone. Similarly, the flexible members described herein could comprise degradable and/or resorbable materials, if desired.

Another particularly useful feature of the various embodiments disclosed herein is the ability of the system to incorporate components constructed from non-ferrous and/or non-magnetic materials (i.e., plastics and/or ceramics). Unlike screw-based fixation, which often requires the use of high strength metals for the screws and/or related components, the components of the present invention could be constructed from virtually any materials, including plastics, ceramics and/or metals, with various plastic components useful in virtually any environment, even where the use of ferrous materials and/or magnetic devices is prohibited (i.e., in high-energy electrical environments and/or near high-strength magnets such as Magnetic Resonance Imaging machines). If visualization of such plastic or ceramic components was desired, such components could include radiopaque elements and/or marker bands, as is well known in the art. In various exemplary embodiments, the bullets and buttons described herein could comprise titanium, stainless steel, PolyEtherEther-Ketone (PEEK) or Poly-L Lactic Acid (PLLA).

Another major advantage of the various embodiment disclosed herein is the ability of the odontoid bullet and button system to accommodate various patients that are not typical surgical candidates for odontoid screw fixation because they may have transverse ligament disruption, anatomical abnormalities and/or misaligned fractured segment and/or communited fractures. The flexibility and size of the odontoid bullet and button system allows it to be used with patients that may not be suitable surgical candidates for odontoid screw fixation because their anatomy interferes with the appropriate screw trajectory (e.g., short neck and barrel-shaped chest patients). Furthermore, the flexibility and size of the odontoid bullet and button system allows it to be used with patients that may not be suitable surgical candidates for odontoid screw fixation because the fractured odontoid and remaining C2 body are misaligned or not horizontal (e.g., the fracture line is not adequately horizontally aligned). Such misalignment may facilitate the use of two or more odontoid bullet and/or button systems.

The embodiments herein describe odontoid fixation components and tools that are relatively inexpensive and easily formed, and are particularly robust in their applications. For example, as described the bullet and button components are unlikely to fail in their intended loading patterns, and the associated flexible fixation members are highly resistant to fatigue fracture (unlike their screw-based counterparts, which can often fracture under repeated loading). Moreover, even where implant removal is required, the present systems components can be easily and readily removed with little or no additional injury to the patient.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A recoverable anchoring system for securing tissue to a bone of a patient through a surgical tunnel formed in the bone, comprising:
   an anchor portion having a generally elongated shape sized and configured to pass completely through the surgical tunnel, the anchor portion having at least one first opening positioned proximate to a midpoint of the generally elongated shape and a second opening positioned proximate to a first end of the anchor portion, the first end of the anchor portion including a tapered end comprising a rounded cone, at least a portion of a side surface of the anchor portion having a curved shape for engagement with an anchor surface portion of the bone proximate to a first end of the surgical tunnel;
   a base portion having a base opening and a side surface for engaging a surface of the tissue proximate to a second end of the surgical tunnel;
   a flexible tension member attached between the anchor portion and the base portion and configured to extend through the surgical tunnel, the flexible tension member configured to extend through the at least one first opening and the base opening and, when tensioned, causes the anchor portion and the base portion to apply a compressive force across at least a portion of the bone and the tissue; and
   a flexible recovery member attached to the second opening of the anchor portion and configured to extend through the surgical tunnel, wherein, when the flexible tension member is severed or released, the flexible recovery member can be tensioned to rotate the anchor portion and draw the anchor portion through the surgical tunnel.

2. The recoverable anchoring system of claim 1, wherein the anchoring system can be deployed into and removed from the bone through a single incision.

3. The recoverable anchoring system of claim 1, wherein the tapered end of the anchor portion includes a reduced width section.

4. The recoverable anchoring system of claim 1, wherein the second opening is located completely within the tapered end of the anchor portion.

5. The recoverable anchoring system of claim 1, wherein the second opening is located at least partially within the reduced width section of the anchor portion.

6. A recoverable anchoring system for securing at least one bone fragment to a bone of a patient through a surgical tunnel formed in the bone, comprising:
   an anchor portion having a generally elongated shape sized and configured to pass completely through the surgical tunnel, the anchor portion having at least one first opening positioned proximate to a midpoint of the generally elongated shape and a second opening positioned proximate to a first end of the anchor portion, the first end of the anchor portion including a generally spherical tapered end at least a portion of a side surface of the anchor portion having a curved shape for engagement with a first surface portion of the at least one bone fragment proximate to a first end of the surgical tunnel;
   a base portion having a base opening and a side surface for engaging a surface of the bone proximate to a second end of the surgical tunnel;
   a flexible tension member attached between the anchor portion and the base portion and configured to extend through the surgical tunnel, the flexible tension member configured to extend through the at least one first opening and the base opening and, when tensioned, causes the anchor portion and the base portion to apply a compressive force across at least a portion of the bone and the at least one bone fragment; and
   a flexible recovery member attached to the second opening of the anchor portion and configured to extend through the surgical tunnel, wherein, when the flexible tension member is severed or released, the flexible recovery member can be tensioned to rotate the anchor portion and draw the anchor portion through the surgical tunnel.

7. The recoverable anchoring system of claim 6, wherein the anchoring system can be deployed into and removed from the bone through a single incision.

8. The recoverable anchoring system of claim 6, wherein the tapered end of the anchor portion is directly adjacent to a reduced height section having an upper generally planar surface and a lower generally planer surface, the second opening comprising a generally tubular passage extending from the upper generally planar surface to the lower generally planer surface, the second opening having a longitudinal length that is less than a longitudinal length of the first opening.

9. The recoverable anchoring system of claim 6, wherein the second opening is located completely within a reduced height section of the anchor portion.

10. The recoverable anchoring system of claim 6, wherein the second opening is located at least partially within a reduced height section of the anchor portion.

* * * * *